United States Patent
Wang

(10) Patent No.: US 12,274,113 B2
(45) Date of Patent: Apr. 8, 2025

(54) HOLE TRANSPORT MATERIAL, QUANTUM DOT LIGHT-EMITTING DEVICE AND MANUFACTURING METHOD THEREOF, AND DISPLAY APPARATUS

(71) Applicant: BOE Technology Group Co., Ltd., Beijing (CN)

(72) Inventor: Haowei Wang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 770 days.

(21) Appl. No.: 17/427,012

(22) PCT Filed: Oct. 28, 2020

(86) PCT No.: PCT/CN2020/124554
§ 371 (c)(1),
(2) Date: Jul. 29, 2021

(87) PCT Pub. No.: WO2022/087926
PCT Pub. Date: May 5, 2022

(65) Prior Publication Data
US 2022/0320453 A1  Oct. 6, 2022

(51) Int. Cl.
*H10K 50/15* (2023.01)
*C07C 57/18* (2006.01)
(Continued)

(52) U.S. Cl.
CPC .............. *H10K 50/15* (2023.02); *C07C 57/18* (2013.01); *C07C 211/09* (2013.01);
(Continued)

(58) Field of Classification Search
CPC ........ H10K 50/15; H10K 50/16; H10K 71/00; H10K 2102/321; H10K 85/6572;
(Continued)

(56) References Cited

U.S. PATENT DOCUMENTS

2019/0305241 A1* 10/2019 Angioni ............... H10K 50/115
2021/0408417 A1* 12/2021 Angioni ................. H10K 50/16

* cited by examiner

*Primary Examiner* — Ruiyun Zhang
(74) *Attorney, Agent, or Firm* — Workman Nydegger

(57) ABSTRACT

The present disclosure provides a hole transport material, a quantum dot light-emitting device and a manufacturing method thereof and a display apparatus. A surface of a quantum dot is modified with a ligand capable of being cross-linked with a modifying group of the hole transport material, that is, a cross-linking group in the ligand, so that when the quantum dot light-emitting device is manufactured, the cross-linking group of the quantum dot material is cross-linked with the modifying group of the hole transport material under a set external stimulus, so that the coupling degree between a light-emitting layer and a hole transport layer is increased and an interface structure between the light-emitting layer and the hole transport layer is weakened, thus facilitating carrier transmission. Under the condition of not sacrificing the transmission rate of electrons, hole injection is increased to the greatest extent, so as to regulate the injection balance of carriers, improve the carrier recombination rate of the quantum dot light-emitting device, and further improve the luminous efficiency and other device performances of the quantum dot light-emitting device. Moreover, the increase of hole injection will reduce the aggregation of carriers at an interface, thereby improving the stability of the device.

7 Claims, 11 Drawing Sheets

(51) Int. Cl.
  *C07C 211/09* (2006.01)
  *C07C 211/54* (2006.01)
  *C07D 209/82* (2006.01)
  *C07D 303/32* (2006.01)
  *C07D 405/06* (2006.01)
  *H10K 50/16* (2023.01)
  *H10K 71/00* (2023.01)
  *B82Y 30/00* (2011.01)
  *H10K 85/60* (2023.01)
  *H10K 102/00* (2023.01)

(52) U.S. Cl.
  CPC .......... *C07C 211/54* (2013.01); *C07D 209/82* (2013.01); *C07D 303/32* (2013.01); *C07D 405/06* (2013.01); *H10K 50/16* (2023.02); *H10K 71/00* (2023.02); *B82Y 30/00* (2013.01); *H10K 85/631* (2023.02); *H10K 85/6572* (2023.02); *H10K 2102/321* (2023.02)

(58) Field of Classification Search
  CPC .. H10K 85/631; C07D 209/82; C07D 303/32; C07C 211/54; B82Y 30/00
  USPC .......................................................... 428/1.1
  See application file for complete search history.

| cathode 500 |
| --- |
| electron transport layer 400 |
| light-emitting layer 300 |
| hole transport layer 200 |
| anode 100 |
| substrate |

Fig. 3A

| anode 100 |
| --- |
| hole transport layer 200 |
| light-emitting layer 300 |
| electron transport layer 400 |
| cathode 500 |
| substrate |

Fig. 3B

HOLE TRANSPORT MATERIAL, QUANTUM DOT LIGHT-EMITTING DEVICE AND MANUFACTURING METHOD THEREOF, AND DISPLAY APPARATUS

CROSS REFERENCE TO RELATED APPLICATIONS

The present disclosure is a US National Stage of International Application No. PCT/CN2020/124554, filed on Oct. 28, 2020, of which the entire contents are incorporated herein by reference.

FIELD

The present disclosure relates to the field of display, in particular to a hole transport material, a quantum dot light-emitting device and a manufacturing method thereof, and a display apparatus.

BACKGROUND

The quantum dot material is an important fluorescent nanomaterial, and has excellent physicochemical and optical properties. For example, it has the advantages of a wide absorption spectrum, a narrow emission spectrum, a high quantum yield and good fluorescence stability. Due to its low-cost solution preparation method, the quantum dot material is widely used in fields such as biological imaging, biosensors, light-emitting diodes (LED) and quantum dot solar cells. The industrial application of quantum dot light-emitting diodes (QLED) requires its high device efficiency. The device efficiency mainly depends on the working state of a quantum dot light-emitting layer. At present, it is generally found that the unbalanced injection rate of electrons and holes into a quantum dot luminescence layer will lead to a charged state of quantum dots, so that non-radiative recombination (Auger recombination) of the electrons and holes is conducted subsequently, which makes the device efficiency generally low.

SUMMARY

An embodiment of the present disclosure provides a hole transport material, including a body of the hole transport material and a modifying group connected with the body of the hole transport material; and the modifying group is configured to be cross-linked with a cross-linking group of a quantum dot material under a set external stimulus.

In a possible implementation mode, in the above hole transport material provided by the embodiment of the present disclosure, the modifying group includes at least one of: a double bond group, a triple bond group or an epoxy group.

In a possible implementation mode, in the above hole transport material provided by the embodiment of the present disclosure, the modifying group includes at least one of: olefin, alkyne, ester group, aldehyde group, carbonyl group, azide, cyano group, amino group, carboxyl group, mercapto group, ethylene oxide, propylene oxide, butylene oxide or pentane oxide.

In a possible implementation mode, in the above hole transport material provided by the embodiment of the present disclosure, the body of the hole transport material includes at least one of: carbazole, triphenylamine, carbazole derivatives or triphenylamine derivatives.

An embodiment of the present disclosure also provides a quantum dot light-emitting device, including an anode, a hole transport layer, a light-emitting layer, an electron transport layer and a cathode disposed in a stacked mode. The hole transport layer includes the hole transport material provided by the embodiment of the present disclosure, and the light-emitting layer includes a quantum dot material including a quantum dot and a ligand connected with the quantum dot; and the ligand includes a coordinating group bonded with the quantum dot, a solubilizing group connected with the coordinating group, and a cross-linking group connected with the solubilizing group, and the cross-linking group is cross-linked with the modifying group of the hole transport material.

In a possible implementation mode, in the quantum dot light-emitting device provided by the embodiment of the present disclosure, the cross-linking group includes at least one of: a double bond group, a triple bond group or an epoxy group.

In a possible implementation mode, in the quantum dot light-emitting device provided by the embodiment of the present disclosure, the cross-linking group includes at least one of: olefin, alkyne, ester group, aldehyde group, carbonyl group, azide, cyano group, amino group, carboxyl group, mercapto group, ethylene oxide, propylene oxide, butylene oxide or pentane oxide.

In a possible implementation mode, in the quantum dot light-emitting device provided by the embodiment of the present disclosure, the solubilizing group includes at least one of: ethyl, n-butyl, tert-butyl, n-octyl, tert-butyl phenyl, methoxy or n-butoxy.

In a possible implementation mode, in the quantum dot light-emitting device provided by the embodiment of the present disclosure, the coordinating group includes at least one of: amino, polyamino, hydroxyl, polyhydroxy, mercapto, polythiol, thioether, polythioether, phosphine or phosphine oxide.

In a possible implementation mode, in the quantum dot light-emitting device provided by the embodiment of the present disclosure, a molecular formula of the ligand of the quantum dot material is as follows:

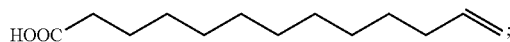

a molecular formula of the hole transport material is as follows:

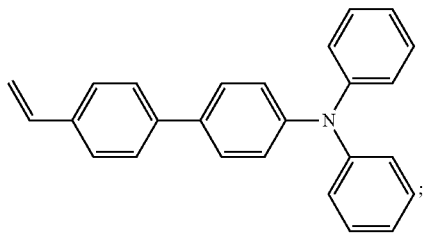 [SMILES: C=Cc1ccc(-c2ccc(N(c3ccccc3)c3ccccc3)cc2)cc1]

and a molecular formula after the ligand of the quantum dot material is cross-linked with the hole transport material is as follows:

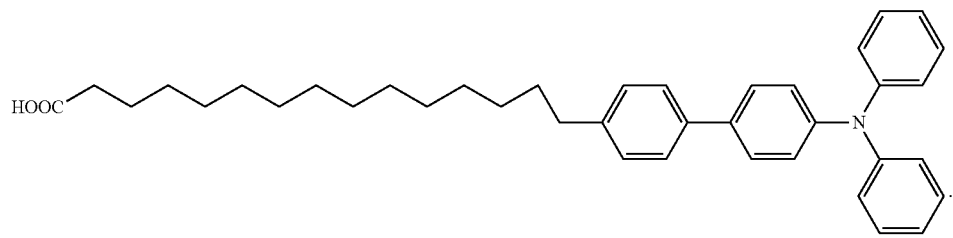 [SMILES: O=C(O)CCCCCCCCCCCCCCc1ccc(-c2ccc(N(c3ccccc3)c3ccccc3)cc2)cc1]

In a possible implementation mode, in the quantum dot light-emitting device provided by the embodiment of the present disclosure, the molecular formula of the ligand of the quantum dot material is as follows:

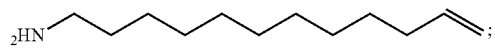

a molecular formula of the hole transport material is as follows:

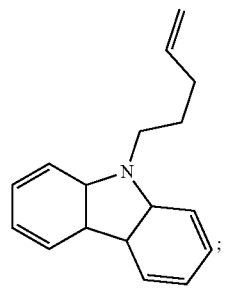 [SMILES: C=CCCCN1C2C=CC=CC2C2C=CC=CC21]

and a molecular formula after the ligand of the quantum dot material is cross-linked with the hole transport material is as follows:

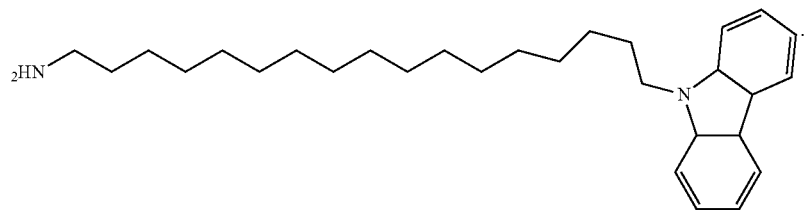

In a possible implementation mode, in the quantum dot light-emitting device provided by the embodiment of the present disclosure, the molecular formula of the ligand of the quantum dot material is as follows:

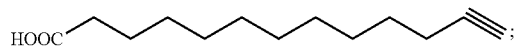

a molecular formula of the hole transport material is as follows:

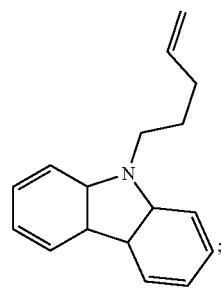 [SMILES: C=CCCCN1C2C=CC=CC2C2C=CC=CC21]

and a molecular formula after the ligand of the quantum dot material is cross-linked with the hole transport material is as follows:

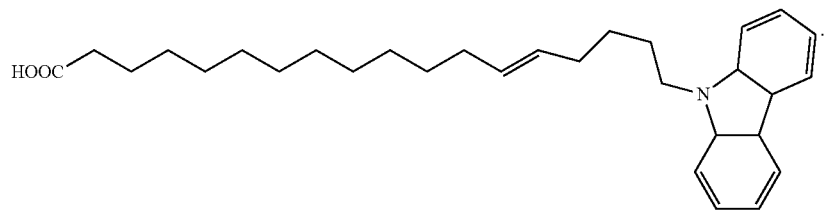 [SMILES: O=C(O)CCCCCCCCCCC/C=C/CCCCN1C2C=CC=CC2C2C=CC=CC21]

In a possible implementation mode, in the quantum dot light-emitting device provided by the embodiment of the present disclosure, a molecular formula of the ligand of the quantum dot material is as follows:

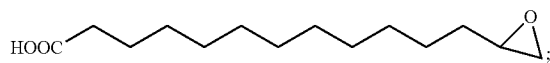 [SMILES: O=C(O)CCCCCCCCCCCC1CO1]

a molecular formula of the hole transport material is as follows:

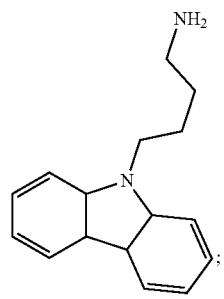 [SMILES: NCCCCN1C2C=CC=CC2C2C=CC=CC21]

and a molecular formula after the ligand of the quantum dot material is cross-linked with the hole transport material is as follows:

In a possible implementation mode, in the quantum dot light-emitting device provided by the embodiment of the present disclosure, a molecular formula of the ligand of the quantum dot material is as follows:

a molecular formula of the hole transport material is as follows:

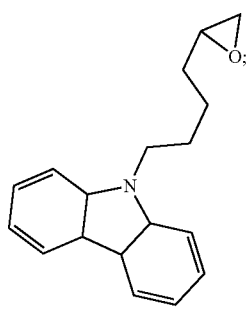

and a molecular formula after the ligand of the quantum dot material is cross-linked with the hole transport material is as follows:

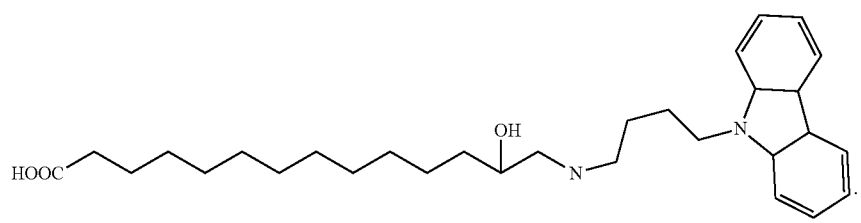 [SMILES: O=C(O)CCCCCCCCCCCC(O)CNCCCCN1C2C=CC=CC2C2C=CC=CC21]

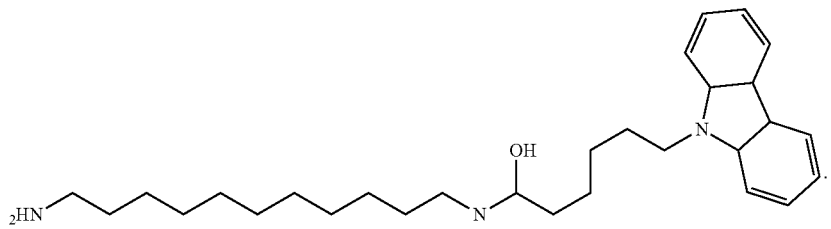

In a possible implementation mode, in the quantum dot light-emitting device provided by the embodiment of the present disclosure, a molecular formula of the ligand of the quantum dot material is as follows:

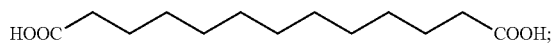

a molecular formula of the hole transport material is as follows:

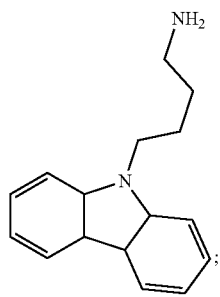 [SMILES: NCCCCN1C2C=CC=CC2C2C=CC=CC21]

and a molecular formula after the ligand of the quantum dot material is cross-linked with the hole transport material is as follows:

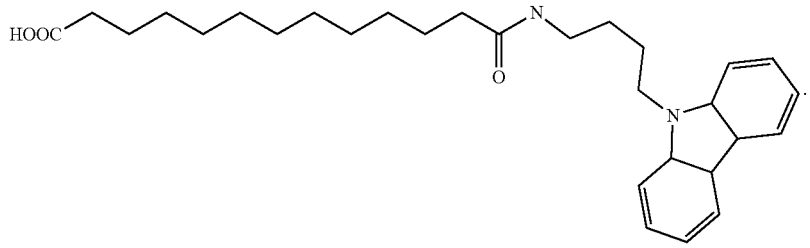 [SMILES: O=C(O)CCCCCCCCCCCC(=O)NCCCCN1C2C=CC=CC2C2C=CC=CC21]

In a possible implementation mode, the quantum dot light-emitting device provided by the embodiments of the present disclosure further includes a substrate, and the anode, the hole transport layer, the light-emitting layer, the electron transport layer and the cathode are sequentially stacked on the substrate.

In a possible implementation mode, the quantum dot light-emitting device provided by the embodiment of the present disclosure further includes a substrate, and the cathode, the electron transport layer, the light-emitting layer, the hole transport layer and the anode are sequentially stacked on the substrate.

An embodiment of the present disclosure also provides a method for manufacturing the quantum dot light-emitting device, including the following steps: forming an anode, a hole transport layer, a light-emitting layer, an electron transport layer and a cathode disposed in a stacked mode, wherein the hole transport layer includes the hole transport material provided by the embodiment of the present disclosure, the light-emitting layer includes a quantum dot material which includes a quantum dot and a ligand connected with the quantum dot, and the ligand includes a coordinating group bonded with the quantum dot, a solubilizing group connected with the coordinating group, and a cross-linking group connected with the solubilizing group; and after the hole transport layer and the light-emitting layer are formed, making the cross-linking group of the quantum dot material cross-linked with the modifying group of the hole transport material by adopting a set external stimulus.

In a possible implementation mode, in the manufacturing method provided by the embodiment of the present disclosure, the external stimulus is ultraviolet irradiation, a wavelength of ultraviolet light is 365 nm or 436 nm, and light intensity of the ultraviolet light ranges from 10 mJ/cm$^2$ to 200 mJ/cm$^2$.

In a possible implementation mode, in the manufacturing method provided by the embodiment of the present disclosure, the external stimulus is an annealing process, a heating temperature of the annealing process ranges from 150° C. to 300° C., and a heating time ranges from 10 min to 60 min.

In a possible implementation mode, the above manufacturing method provided by the embodiment of the present disclosure further includes:

forming the cathode on a substrate;
forming the electron transport layer on the cathode;
forming the light-emitting layer on the electron transport layer;
forming the hole transport layer on the light-emitting layer;
making the cross-linking group of the quantum dot material cross-linked with the modifying group of the hole transport material by adopting the set external stimulus; and
forming the anode on the hole transport layer.

In a possible implementation mode, the above manufacturing method provided by the embodiment of the present disclosure further includes:

forming the anode on a substrate;

forming the hole transport layer on the anode;

forming the light-emitting layer on the hole transport layer;

making the cross-linking group of the quantum dot material cross-linked with the modifying group of the hole transport material by adopting the set external stimulus;

forming the electron transport layer on the light-emitting layer; and forming the cathode on the electron transport layer.

In a possible implementation mode, specifically, in the above manufacturing method provided by the embodiment of the present disclosure:

forming the light-emitting layer on the hole transport layer specifically includes:

forming a monochromatic light-emitting layer on the hole transport layer by adopting a monochromatic quantum dot material;

and making the cross-linking group of the quantum dot material cross-linked with the modifying group of the hole transport material by adopting the set external stimulus specifically includes:

irradiating a corresponding area of the monochromatic light-emitting layer with ultraviolet light under the shielding of a mask plate, to enable the cross-linking group of the monochromatic quantum dot material in the corresponding area to be cross-linked with the modifying group of the hole transport material; and cleaning the monochromatic light-emitting layer, and obtaining a graphical monochromatic light-emitting layer by removing an area shielded by the mask plate.

An embodiment of the present disclosure also provides a display apparatus, including the quantum dot light-emitting device provided by the embodiments of the present disclosure.

BRIEF DESCRIPTION OF THE DRAWINGS

FIG. 3A is a schematic structural diagram of a quantum dot light-emitting device provided by an embodiment of the present disclosure.

FIG. 3B is a schematic structural diagram of a quantum dot light-emitting device provided by an embodiment of the present disclosure.

DETAILED DESCRIPTION OF THE EMBODIMENTS

Figure 1:
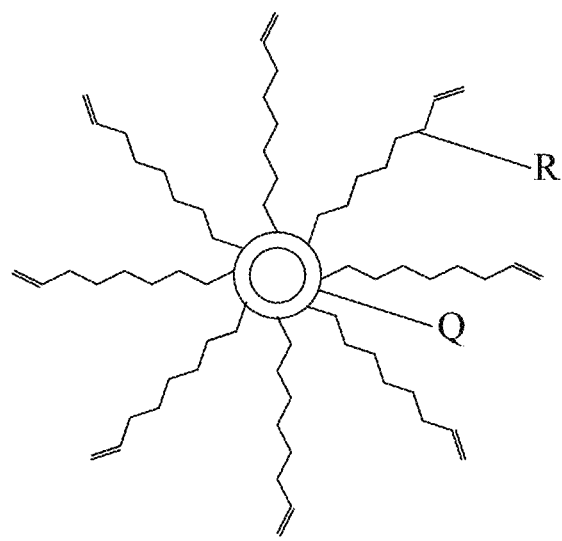
FIG. 1 is a schematic structural diagram of a quantum dot material provided by an embodiment of the present disclosure.

In a typical quantum dot light-emitting diode structure, a quantum dot light-emitting layer is between an electron transport layer and a hole transport layer. The transmission speed of charge carriers (electrons and holes) mainly depends on the electrical properties of the electron transport layer and the hole transport layer. However, in QLED devices, the transmission rate of electrons is higher than that of holes, thereby leading to the imbalance of carrier injection and further leads to the performance degradation of QLEDs.

On this basis, the present disclosure designs a hole transport material, quantum dot material and quantum dot light-emitting device for adjusting the transmission rate balance of carriers (electrons or holes). A surface of a body of the hole transport material is modified with groups, and a surface of a quantum dot is modified with a ligand capable of being cross-linked with the hole transport material, which increases the coupling degree between the quantum dot light-emitting layer and the hole transport layer, promotes hole injection, regulates carrier injection balance, and further improves the luminous efficiency and other device performances of QLED devices.

In order to make the object, technical solution and advantages of the present disclosure clearer, the present disclosure will be described in further detail below with reference to the accompanying drawings. Obviously, the described embodiments are only a part of the embodiments of the present disclosure, not all of the embodiments. Based on the embodiments in the present disclosure, all other embodiments obtained by those of ordinary skill in the art without creative labor are within the scope of protection of the present disclosure.

The shapes and sizes of the components in the drawings do not reflect true proportions, and are only for the purpose of schematically illustrating the present disclosure.

An embodiment of the present disclosure provides a hole transport material, including a body of the hole transport material and a modifying group connected with the body of the hole transport material, and the modifying group is configured to be cross-linked with a cross-linking group of a quantum dot material under a set external stimulus.

Correspondingly, as shown in FIG. 1, an embodiment of the present disclosure provides a quantum dot material, including a quantum dot Q and a ligand R connected with the quantum dot.

Figure 2:
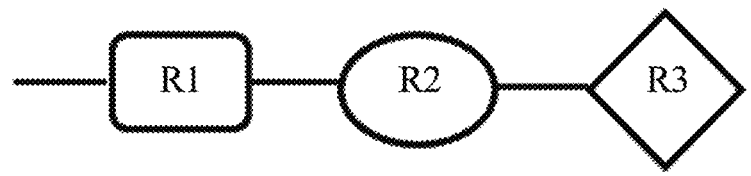
FIG. 2 is a schematic structural diagram of a ligand in a quantum dot material provided by an embodiment of the present disclosure.

As shown in FIG. 2, the ligand includes a coordinating group R1 bonded with the quantum dot, a solubilizing group R2 connected with the coordinating group R1, and a cross-linking group R3 connected with the solubilizing group R2. The cross-linking group R3 is configured to be cross-linked with the modifying group of the hole transport material under a set external stimulus.

Specifically, in the above-mentioned hole transport material and quantum dot material provided by the embodiments of this disclosure, a surface of the quantum dot is modified with the ligand capable of being cross-linked with the modifying group of the hole transport material, that is, the cross-linking group R3 in the ligand, so that when the above-mentioned hole transport material and quantum dot material provided in the embodiments of the present disclosure are used to make a light-emitting layer of a quantum dot light-emitting device, the cross-linking group R3 of the quantum dot material can be cross-linked with the modifying group of the hole transport material under the set external stimulus, which increases the coupling degree between the light-emitting layer and the hole transport layer and weakens an interface structure between the light-emitting layer and the hole transport layer, thus facilitating carrier transmission. Under the condition of not sacrificing the transmission rate of electrons, hole injection is increased to the greatest extent, so as to regulate the injection balance of carriers, improve the carrier recombination rate of the quantum dot light-emitting device, and further improve the luminous efficiency and other device performances of the quantum dot light-emitting device. Moreover, the increase of hole injection will reduce the aggregation of carriers at an interface, thereby improving the stability of the device.

Specifically, the cross-linking between the hole transport layer and the light-emitting layer will not cause the energy level change of the light-emitting layer and the hole transport layer, instead, it makes the energy level change between the light-emitting layer and the hole transport layer more gentle, thus being beneficial to hole transmission. Further, cross-linking may occur between the cross-linking groups of quantum dot materials, that is, cross-linking exists between the quantum dot materials. After cross-linking between the quantum dot materials, connection by chemical bonds is conducive to carrier transmission between the quantum dot materials.

Specifically, in the above-mentioned hole transport material and quantum dot material provided in the embodiments of the present disclosure, in order to cross-link the hole transport layer and the light-emitting layer, the modified group of the hole transport material and the cross-linking group R3 of the quantum dot material can be double bond group, triple bond group, epoxy group, etc., and specifically can be olefin, alkyne, ester group, aldehyde group, carbonyl group, azide, cyano group, amino group, carboxyl group, mercapto group, ethylene oxide, propylene oxide, butylene oxide and pentane oxide. The hole transport material can be a small molecule hole cross-linking material, which can specifically include carbazole, triphenylamine, carbazole derivatives and triphenylamine derivatives.

Optionally, in the quantum dot material provided by the embodiment of the present disclosure, the quantum dots are generally inorganic quantum dots. The inorganic quantum dots can be CdS, CdSe, CdTe, ZnSe, InP, PbS, CuInS2, ZnO, CsPbCl3, CsPbBr3, CsPbI3, CdS/ZnS, CdSe/ZnS, ZnTe, InP/ZnS, PbS/ZnS, InAs, InGaAs, InGaN, GaN, ZnTe, Si, Ge, C and other nano-scale materials with the above components, such as nanorod materials.

Specifically, from the perspective of environmental protection, the inorganic quantum dots can optionally be cadmium-free quantum dots, so that the harm of heavy metal cadmium to the environment and human body can be avoided, and heavy metal pollution can be effectively avoided. Of course, the inorganic quantum dots can also be cadmium-containing quantum dots when the problem of heavy metal pollution does not need to be considered, which is not limited here.

Optionally, in the above quantum dot material provided by the embodiment of the present disclosure, the coordinating group R1 is to bond with the surface of the quantum dot, and the coordinating group R1 may include at least one of the following functional groups or elements which can be bonded with the surface of the quantum dot, such as amino, polyamino, hydroxyl, polyhydroxy, sulfydryl, polysulfydryl, thioether, polythioether, phosphine and phosphine oxide.

Optionally, in the quantum dot material provided by the embodiment of the present disclosure, the solubilizing group R2 may include at least one of the following: ethyl, n-butyl, tert-butyl, n-octyl, tert-butyl phenyl, methoxy, n-butoxy, etc.

Optionally, in the quantum dot material provided by the embodiment of the present disclosure, the cross-linking group R3 may include at least one of the following: double bond group, triple bond group, epoxy group, and the like.

Optionally, in the quantum dot material provided in the embodiment of the present disclosure, the cross-linking group R3 may specifically include at least one of the following: olefin, alkyne, ester group, aldehyde group, carbonyl group, azide, cyano group, amino group, carboxyl group, mercapto group, ethylene oxide, propylene oxide, butylene oxide, pentane oxide, etc.

Specifically, the quantum dot material provided by embodiment of the present disclosure can be applied to semiconductor apparatuses, display apparatuses, quantum dot display apparatuses, light-emitting apparatuses, magnetic induction and fluorescence induction apparatuses, and the like.

Based on the same inventive concept, an embodiment of the present disclosure also provides a quantum dot light-emitting device. Since the principle of solving problems of the quantum dot light-emitting device is similar to that of the aforementioned hole transport material and quantum dot material, one can refer to the implementation of the hole transport material and quantum dot material for the implementation of the quantum dot light-emitting device, which will not be repeated here.

Specifically, as shown in FIGS. 3A and 3B, the quantum dot light-emitting device includes an anode 100, a hole transport layer 200, a light-emitting layer 300, an electron transport layer 400 and a cathode 500 disposed in a stacked mode. The light-emitting layer 300 includes the above-mentioned quantum dot material provided by the embodiment of the present disclosure, and the hole transport layer 200 includes the above-mentioned hole transport material provided by the embodiment of the present disclosure. The cross-linking group of the quantum dot material is cross-linked with the modifying group of hole transport material. In other words, the quantum dot light-emitting device described in the embodiment of the present disclosure has a cross-linking product of the cross-linking group and the modifying group of the hole transport material at an interface between the hole transport layer and the light-emitting layer. FIG. 3A is an upright structure of the device, that is, the anode 100, the hole transport layer 200, the light-emitting layer 300, the electron transport layer 400 and the cathode 500 are sequentially formed on a substrate. FIG. 3B is an inverted structure of the device, that is, the cathode 500, the electron transport layer 400, the light-emitting layer 300, the hole transport layer 200 and the anode 100 are sequentially formed on a substrate. In addition, the quantum dot light-emitting device provided by the embodiment of the present disclosure may also include other functional films, such as a hole injection layer, which will not be described in detail here.

Specifically, in the quantum dot light-emitting device provided by the embodiment of the present disclosure, after the cross-linking group R3 of the quantum dot material is cross-linked with the modifying group on a surface of the hole transport material, the coupling degree between the light-emitting layer and the hole transport layer is increased, and an interface structure between the light-emitting layer and the hole transport layer is weakened, which is beneficial to carrier transmission. Under the condition of not sacrificing the transmission rate of electrons, hole injection is increased to the greatest extent, so as to regulate the injection balance of carriers, improve the carrier recombination rate of the quantum dot light-emitting device, and further improve the luminous efficiency and other device performances of the quantum dot light-emitting device. Moreover, the increase of hole injection will reduce the aggregation of carriers at an interface, thereby improving the stability of the device.

Specifically, the cross-linking between the hole transport layer and the light-emitting layer will not cause the energy level change of the light-emitting layer and the hole transport layer, instead, it makes the energy level change between the light-emitting layer and the hole transport layer more gentle, thus being beneficial to hole transmission. Further, cross-linking may occur between the cross-linking groups of quantum dot materials (for example, when the cross-linking groups of the quantum dot materials include olefin and alkyne), that is, cross-linking exists between the quantum dot materials. After cross-linking between the quantum dot materials, connection by chemical bonds is conducive to carrier transmission between the quantum dot materials.

Correspondingly, the hole transport material can be made from a triphenylamine derivative, and its molecular formula is as follows, where the triphenylamine group has strong electron binding ability, styrene linked with the triphenylamine group forms the modification group, and the carbon-carbon double bond in the modification group can be cross-linked with the quantum dot material ligand:

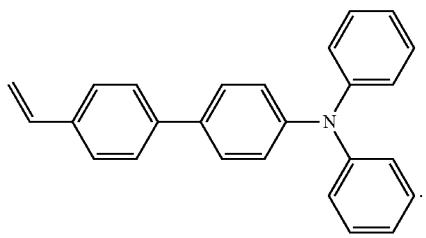 [SMILES: C=Cc1ccc(-c2ccc(N(c3ccccc3)c3ccccc3)cc2)cc1]

Figure 4:
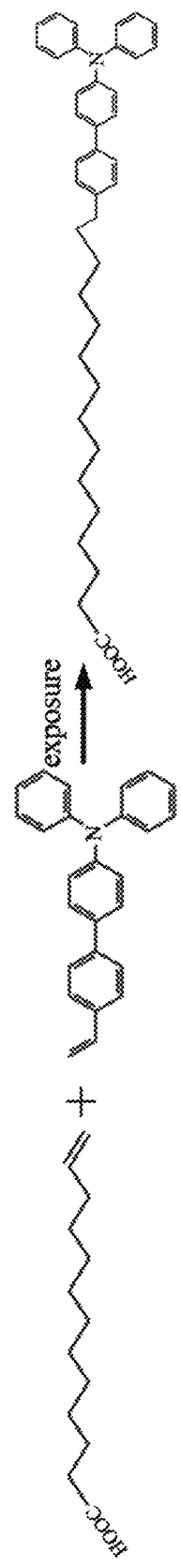
FIG. 4 is a schematic diagram of a cross-linking reaction in a quantum dot light-emitting device provided by an embodiment of the present disclosure.

Specifically, the quantum dot material and the hole transport material can be cross-linked by annealing or ultraviolet irradiation; for example, under the irradiation of G line or I line, the carbon-carbon double bond of the quantum dot ligand and a carbon-carbon double bond of the triphenylamine derivative are broken and then cross-linked; after cross-linking, the light-emitting layer and the hole transport layer are linked by chemical bonds, which greatly improves the transmission efficiency of holes between the hole transport layer and the light-emitting layer; the cross-linking reaction formula of the ligand of the quantum dot material and the hole transport material is shown in FIG. 4; and the molecular formula after the ligand of the quantum dot material is cross-linked with the hole transport material is as follows:

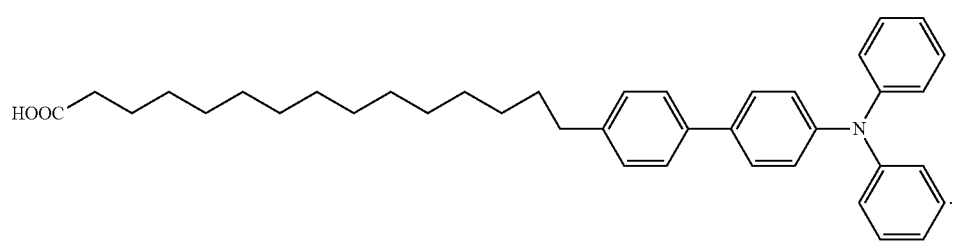 [SMILES: O=C(O)CCCCCCCCCCCCCCc1ccc(-c2ccc(N(c3ccccc3)c3ccccc3)cc2)cc1]

Further, in the quantum dot light-emitting device provided by the embodiment of the present disclosure, the cross-linking group of the quantum dot material and the modifying group of the hole transport material can be interchanged, and the specific materials in the quantum dot light-emitting device provided by the embodiment of the present disclosure will be explained by specific examples below.

Optionally, in the quantum dot light-emitting device provided by the embodiment of the present disclosure, the molecular formula of the ligand of the quantum dot material is as follows, where the carboxyl group is the coordinating group bonded with the quantum dot, and the cross-linking group is a carbon-carbon double bond arranged at the end of the quantum dot ligand for being cross-linked with the hole transport material:

For another example, optionally, in the quantum dot light-emitting device provided by the embodiment of the present disclosure, the molecular formula of the ligand of the quantum dot material is as follows, where amino is the coordinating group bonded with the quantum dot, and the cross-linking group is a carbon-carbon double bond arranged at the end of the quantum dot ligand for being cross-linked with the hole transport material:

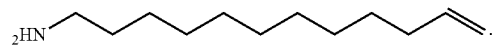

Correspondingly, the hole transport material can be made from carbazole derivatives, and its molecular formula is as follows, where the carbazole group has strong electron

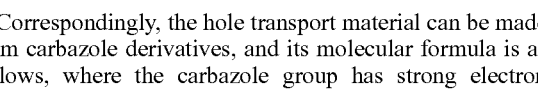

binding ability, pentene linked with the carbazole group forms the modification group, and the carbon-carbon double bond in the modification group can be cross-linked with the quantum dot material ligand:

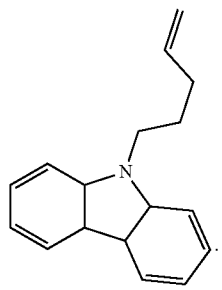 [SMILES: C=CCCCN1C2C=CC=CC2C2C=CC=CC21]

Figure 5:
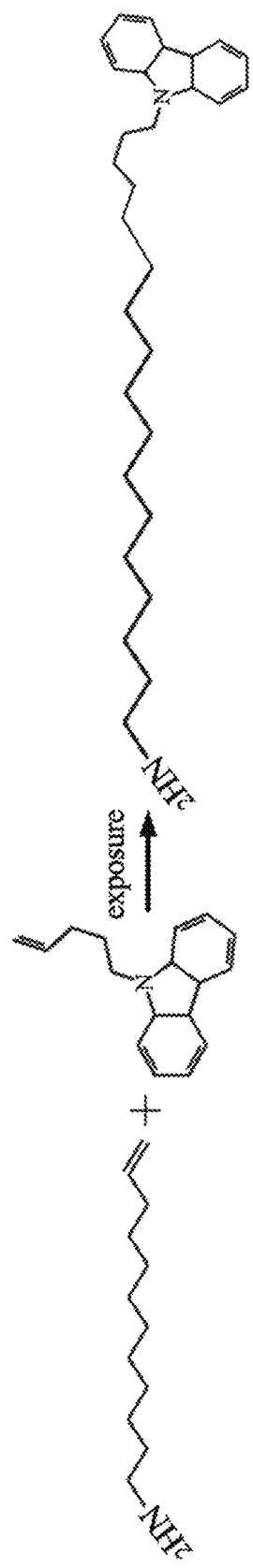
FIG. 5 is a schematic diagram of another cross-linking reaction in a quantum dot light-emitting device provided by an embodiment of the present disclosure.

Specifically, the quantum dot material and the hole transport material can be cross-linked by annealing or ultraviolet irradiation; for example, under the irradiation of G line or I line, the carbon-carbon double bond of the quantum dot ligand and a carbon-carbon double bond of the carbazole derivative are broken and then cross-linked; after cross-linking, the light-emitting layer and the hole transport layer are linked by chemical bonds, which greatly improves the transmission efficiency of holes between the hole transport layer and the light-emitting layer; the cross-linking reaction formula of the ligand of the quantum dot material and the hole transport material is shown in FIG. 5; and the molecular formula after the ligand of the quantum dot material is cross-linked with the hole transport material is as follows:

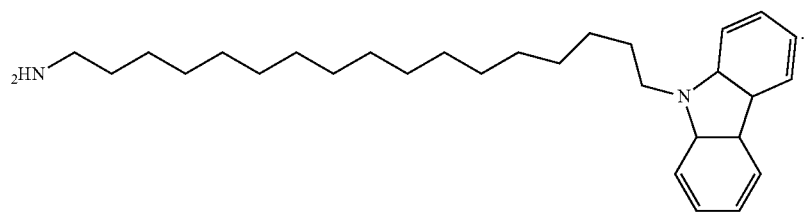

For another example, optionally, in the quantum dot light-emitting device provided by the embodiment of the present disclosure, the molecular formula of the ligand of the quantum dot material is as follows, where the carboxyl group is the coordinating group bonded with the quantum dot, and the cross-linking group is a carbon-carbon triple bond arranged at the end of the quantum dot ligand for being cross-linked with the hole transport material:

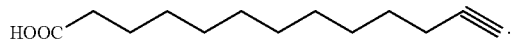

Correspondingly, the hole transport material can be made from carbazole derivatives, and its molecular formula is as follows, where the carbazole group has strong electron binding ability, pentene linked with the carbazole group forms the modification group, and the carbon-carbon double bond in the modification group can be cross-linked with the quantum dot material ligand:

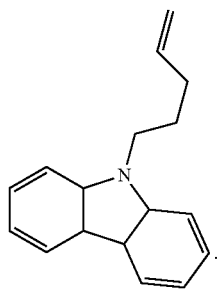 [SMILES: C=CCCCN1C2C=CC=CC2C2C=CC=CC21]

Figure 6:
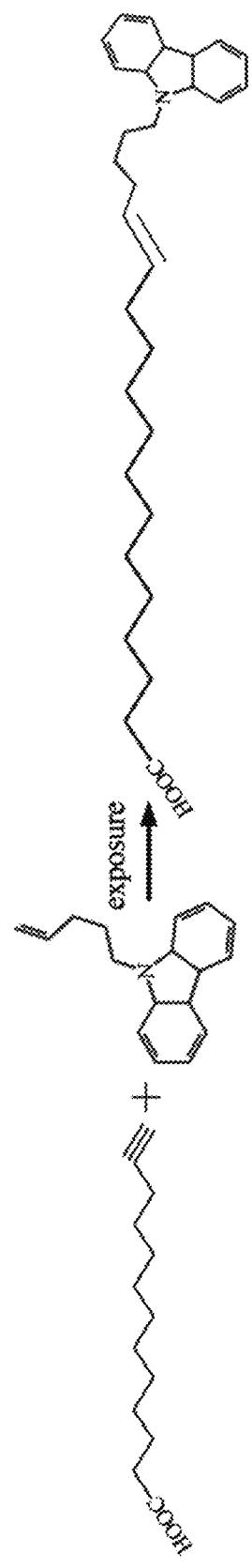
FIG. 6 is a schematic diagram of further cross-linking reaction in a quantum dot light-emitting device provided by an embodiment of the present disclosure.

Specifically, the quantum dot material and the hole transport material can be cross-linked by annealing or ultraviolet irradiation; for example, under the irradiation of G line or I line, the carbon-carbon triple bond of the quantum dot ligand and a carbon-carbon double bond of the carbazole derivative are broken and then cross-linked; after cross-linking, the light-emitting layer and the hole transport layer are linked by chemical bonds, which greatly improves the transmission efficiency of holes between the hole transport layer and the light-emitting layer; the cross-linking reaction formula of the ligand of the quantum dot material and the hole transport material is shown in FIG. 6; and the molecular formula after the ligand of the quantum dot material is cross-linked with the hole transport material is as follows:

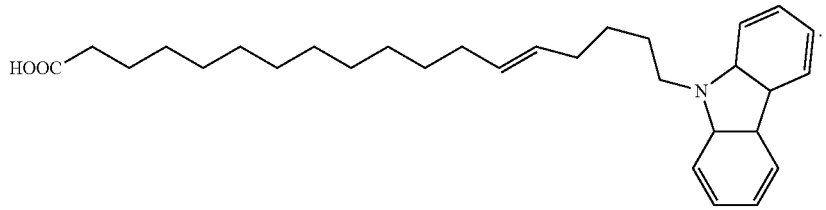 [SMILES: O=C(O)CCCCCCCCCCC/C=C/CCCCN1C2C=CC=CC2C2C=CC=CC21]

For another example, optionally, in the quantum dot light-emitting device provided by the embodiment of the present disclosure, the molecular formula of the ligand of the quantum dot material is as follows, where the carboxyl group is the coordinating group bonded with the quantum dot, and the cross-linking group is an epoxy group arranged at the end of the quantum dot ligand for being cross-linked with the hole transport material:

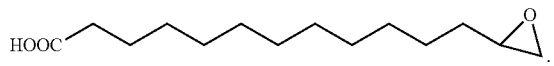 [SMILES: O=C(O)CCCCCCCCCCCC1CO1]

Correspondingly, the hole transport material can be made from carbazole derivatives, and its molecular formula is as follows, where the carbazole group has strong electron binding ability, amino linked with the carbazole group forms the modification group, and the amino in the modification group can be cross-linked with the quantum dot material ligand:

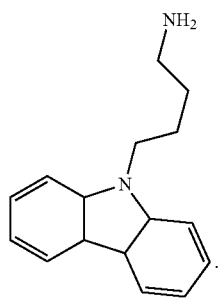 [SMILES: NCCCCN1C2C=CC=CC2C2C=CC=CC21]

Figure 7:
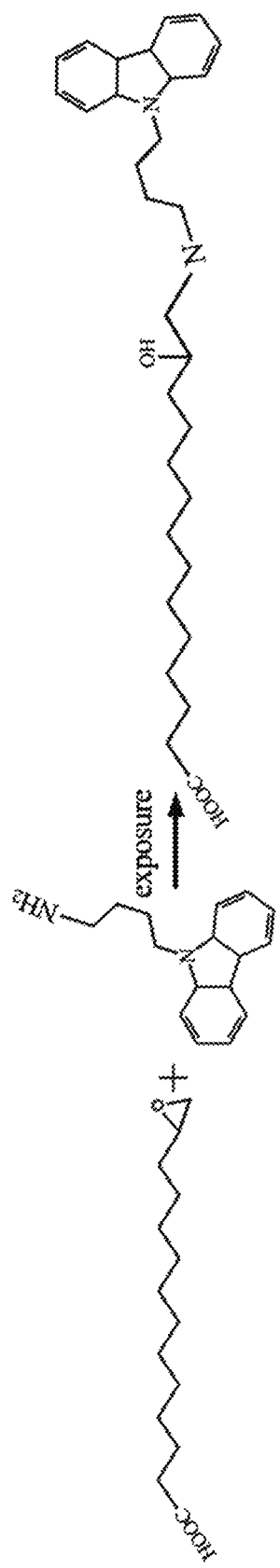
FIG. 7 is a schematic diagram of yet further cross-linking reaction in a quantum dot light-emitting device provided by an embodiment of the present disclosure.

Specifically, the quantum dot material and the hole transport material can be cross-linked by annealing or ultraviolet irradiation; for example, under the irradiation of G line or I line, the epoxy group of the quantum dot ligand and the amino of the carbazole derivative are broken and then cross-linked; after cross-linking, the light-emitting layer and the hole transport layer are linked by chemical bonds, which greatly improves the transmission efficiency of holes between the hole transport layer and the light-emitting layer; the cross-linking reaction formula of the ligand of the quantum dot material and the hole transport material is shown in FIG. 7; and the molecular formula after the ligand of the quantum dot material is cross-linked with the hole transport material is as follows:

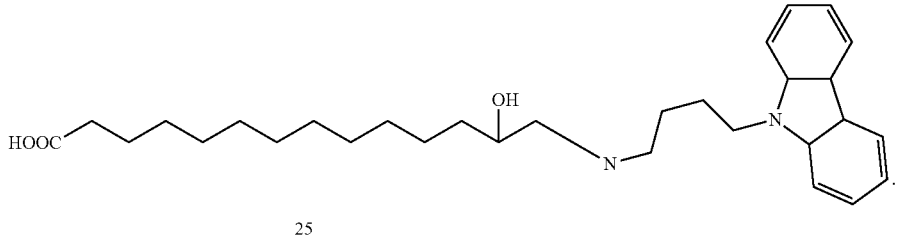

For another example, optionally, in the quantum dot light-emitting device provided by the embodiment of the present disclosure, the molecular formula of the ligand of the quantum dot material is as follows, where amino is the coordinating group bonded with the quantum dot, and the cross-linking group is amino arranged at the end of the quantum dot ligand for being cross-linked with the hole transport material:

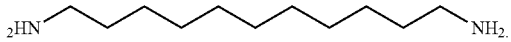

Correspondingly, the hole transport material can be made from carbazole derivatives, and its molecular formula is as follows, where the carbazole group has strong electron binding ability, the epoxy group linked with the carbazole group forms the modification group, and the epoxy group in the modification group can be cross-linked with the quantum dot material ligand:

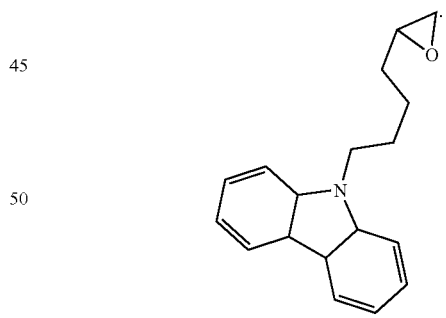

Figure 8:
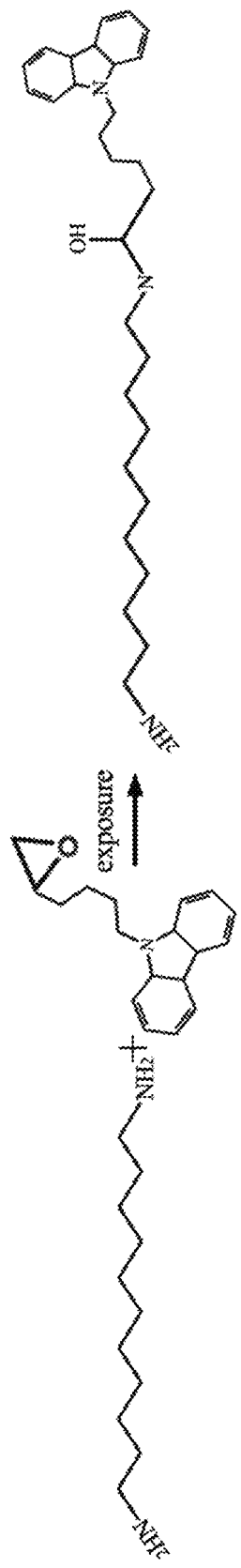
FIG. 8 is a schematic diagram of further another cross-linking reaction in a quantum dot light-emitting device provided by an embodiment of the present disclosure.

Specifically, the quantum dot material and the hole transport material can be cross-linked by annealing or ultraviolet irradiation; for example, under the irradiation of G line or I line, amino of the quantum dot ligand and the epoxy group of the carbazole derivative are broken and then cross-linked; after cross-linking, the light-emitting layer and the hole transport layer are linked by chemical bonds, which greatly improves the transmission efficiency of holes between the hole transport layer and the light-emitting layer; the cross-linking reaction formula of the ligand of the quantum dot material and the hole transport material is shown in FIG. 8; and the molecular formula after the ligand of the quantum dot material is cross-linked with the hole transport material is as follows:

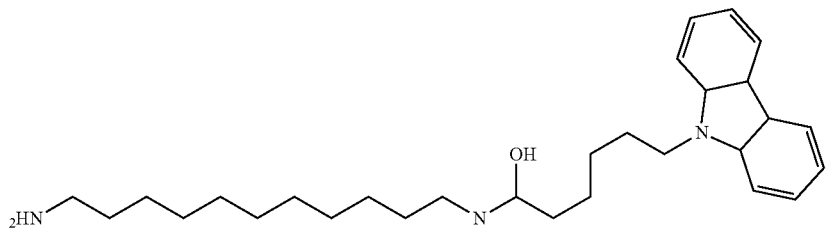

For another example, optionally, in the quantum dot light-emitting device provided by the embodiment of the present disclosure, the molecular formula of the ligand of the quantum dot material is as follows, where the carboxyl group is the coordinating group bonded with the quantum dot, and the cross-linking group is the carboxyl group arranged at the end of the quantum dot ligand for being cross-linked with the hole transport material:

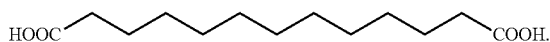 [SMILES: O=C(O)CCCCCCCCCCCC(=O)O]

Correspondingly, the hole transport material can be made from carbazole derivatives, and its molecular formula is as follows, where the carbazole group has strong electron binding ability, amino linked with the carbazole group forms the modification group, and the amino in the modification group can be cross-linked with the quantum dot material ligand:

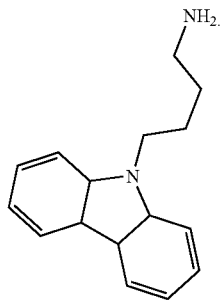 [SMILES: NCCCCN1C2C=CC=CC2C2C=CC=CC21]

Figure 9:
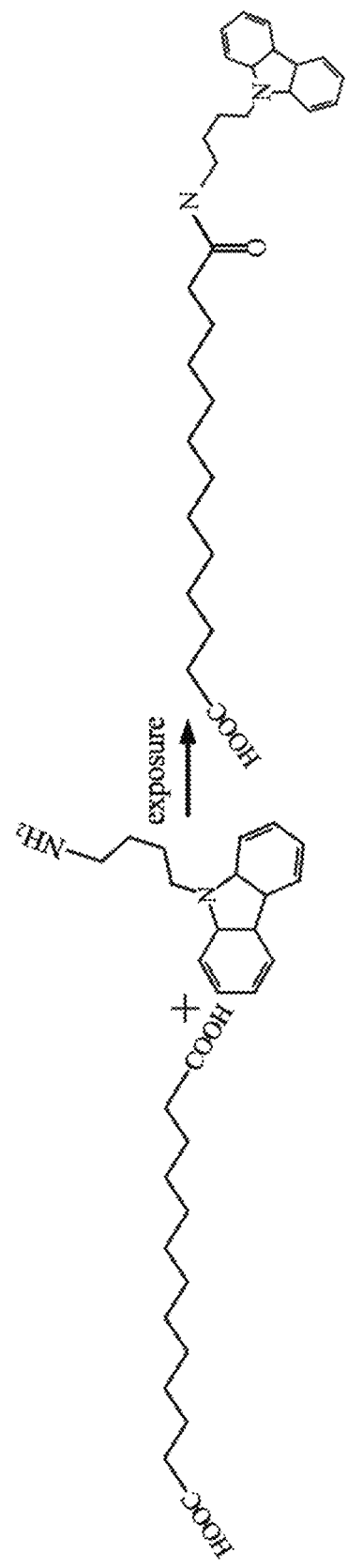
FIG. 9 is a schematic diagram of further another cross-linking reaction in a quantum dot light-emitting device provided by an embodiment of the present disclosure.

Specifically, the quantum dot material and the hole transport material can be cross-linked by annealing or ultraviolet irradiation; for example, under the irradiation of G line or I line, the carboxyl group of the quantum dot ligand and the amino of the carbazole derivative are broken and then cross-linked; after cross-linking, the light-emitting layer and the hole transport layer are linked by chemical bonds, which greatly improves the transmission efficiency of holes between the hole transport layer and the light-emitting layer; the cross-linking reaction formula of the ligand of the quantum dot material and the hole transport material is shown in FIG. 9; and the molecular formula after the ligand of the quantum dot material is cross-linked with the hole transport material is as follows:

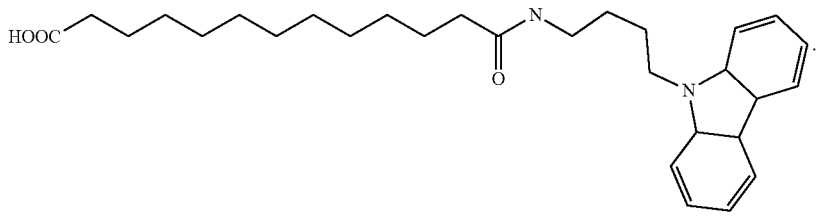 [SMILES: O=C(O)CCCCCCCCCCCC(=O)NCCCCN1C2C=CC=CC2C2C=CC=CC21]

Figure 10:
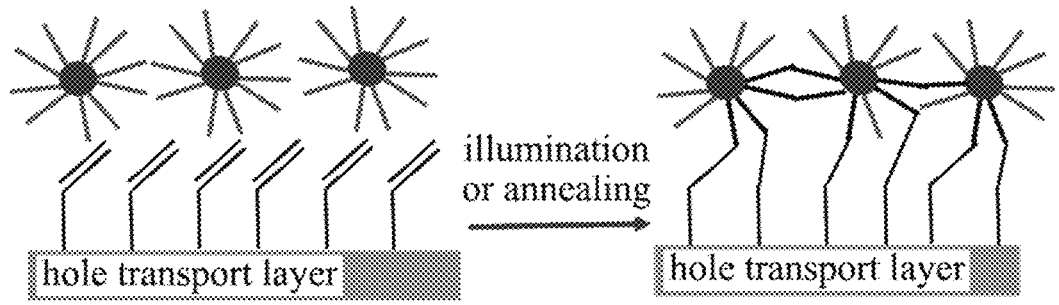
FIG. 10 is a schematic diagram of cross-linking of a light-emitting layer and a hole transport layer during manufacturing of a quantum dot light-emitting device provided by an embodiment of the present disclosure.

Based on the same inventive concept, an embodiment of the present disclosure also provides a manufacturing method of a quantum dot light-emitting device, including:

an anode, a hole transport layer, a light-emitting layer, an electron transport layer and a cathode disposed in a stacked mode are formed, wherein the light-emitting layer includes the above-mentioned quantum dot material provided in the embodiment of the present disclosure, and the hole transport layer includes the above-mentioned hole transport material provided by the embodiment of the present disclosure; and after the hole transport layer and the light-emitting layer are formed, as shown in FIG. 10, the cross-linking group of the quantum dot material is made to be cross-linked with the modifying group of the hole transport material by adopting a set external stimulus.

Optionally, in the above manufacturing method provided by the embodiment of the present disclosure, the external stimulus may be ultraviolet irradiation, the exposure time is adjusted according to the exposure amount per second of different exposure machines, the wavelength of the ultraviolet light for exposure is 365 nm or 436 nm, and the light intensity of the ultraviolet light ranges from 10 mJ/cm$^2$ to 200 mJ/cm$^2$.

Or, optionally, in the above manufacturing method provided by the embodiment of the present disclosure, the external stimulus may be an annealing process, and the heating temperature of the annealing process ranges from 150° C. to 300° C. and the heating time ranges from 10 min to 60 min according to different cross-linking materials and cross-linking groups.

Figure 11:
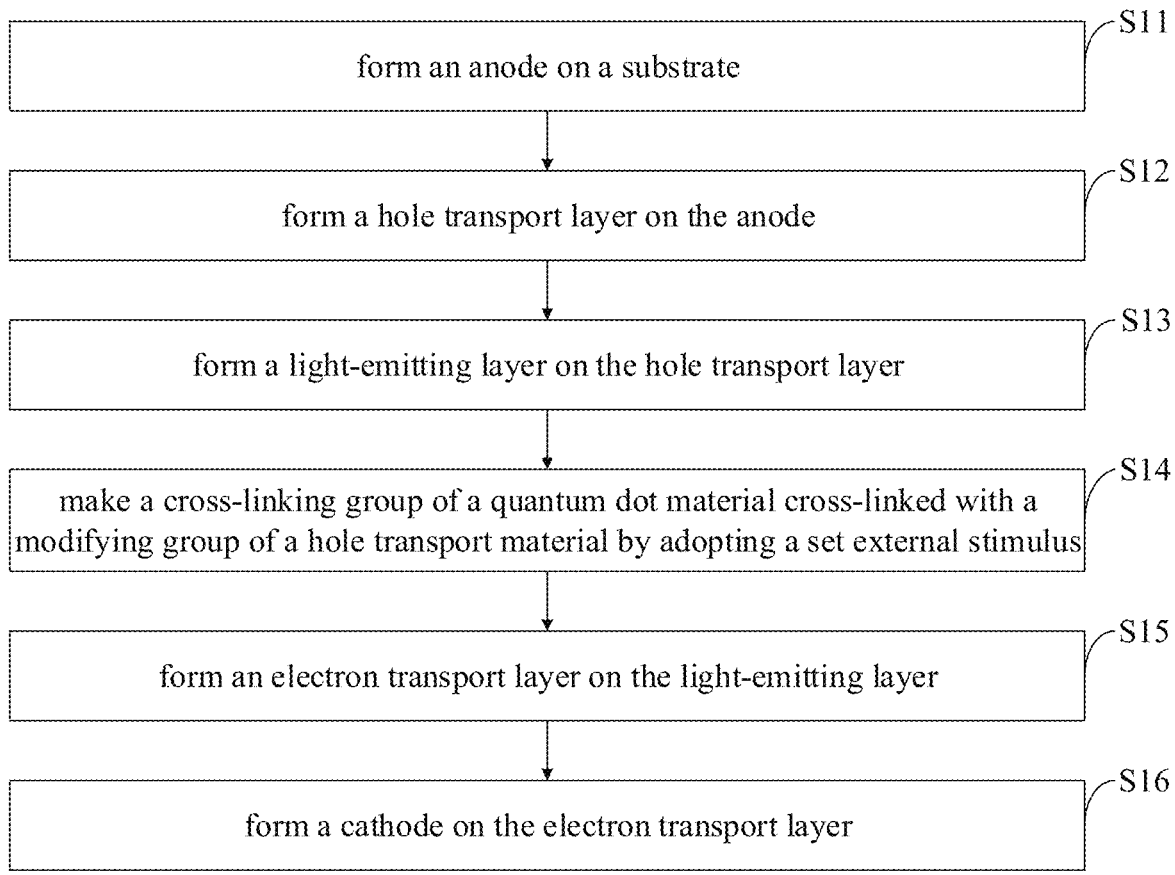
FIG. 11 is a specific flow diagram of a manufacturing method of a quantum dot light-emitting device provided by an embodiment of the present disclosure.

Specifically, the manufactured quantum dot light-emitting device may adopt the upright structure as shown in FIG. 3A, and its manufacturing process is shown in FIG. 11, which specifically includes the following steps:

S11, the anode is formed on a substrate.

S12, the hole transport layer is formed on the anode.

S13, the light-emitting layer is formed on the hole transport layer.

S14, the cross-linking group of the quantum dot material is cross-linked with the modifying group of the hole transport material by adopting the set external stimulus.

S15, the electron transport layer is formed on the light-emitting layer.

S16, the cathode is formed on the electron transport layer.

Figure 12:
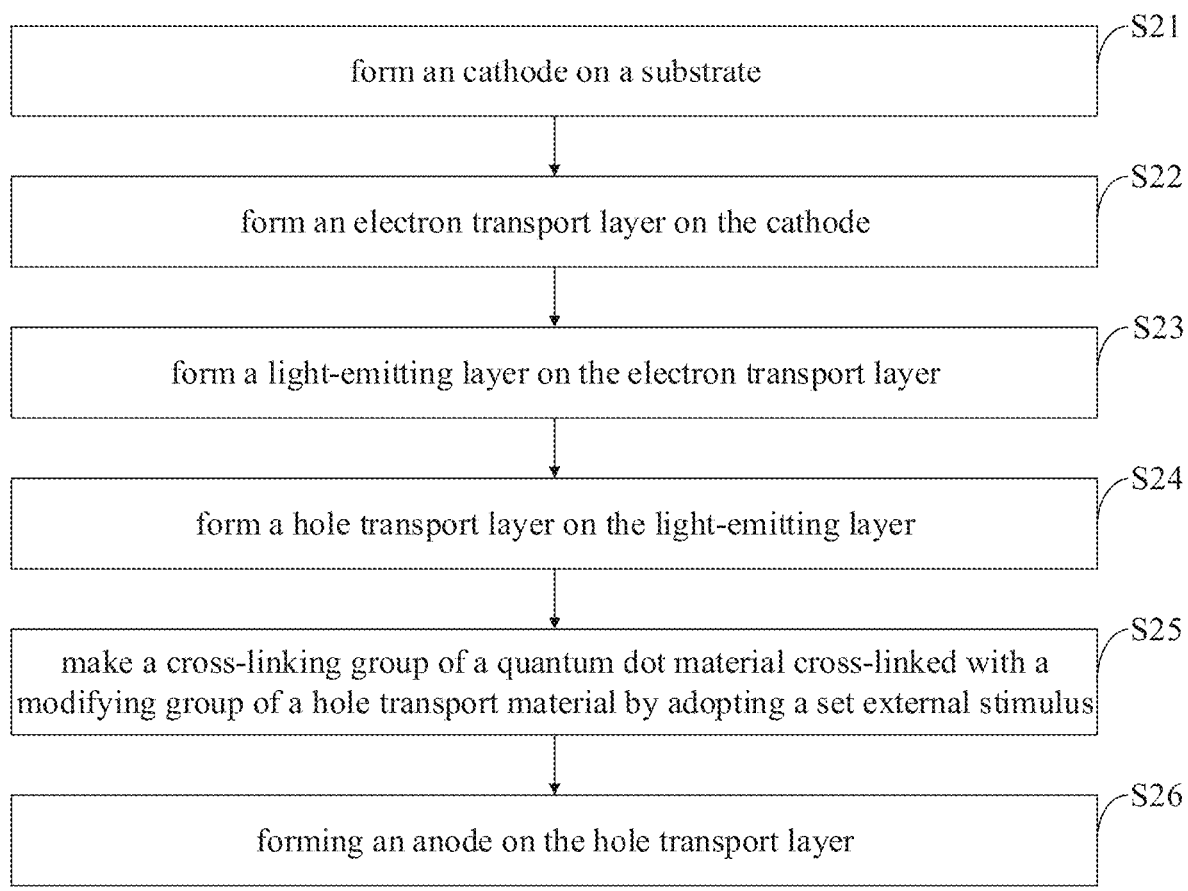
FIG. 12 is another specific flow diagram of a manufacturing method of a quantum dot light-emitting device provided by an embodiment of the present disclosure.

Specifically, the manufactured quantum dot light-emitting device can adopt the inverted structure as shown in FIG. 3B, and its manufacturing process is shown in FIG. 12, which specifically includes the following steps.

S21, the cathode is formed on a substrate.

S22, the electron transport layer is formed on the cathode.

S23, the light-emitting layer is formed on the electron transport layer.

S24, the hole transport layer is formed on the light-emitting layer.

S25, the cross-linking group of the quantum dot material is cross-linked with the modifying group of the hole transport material by adopting the set external stimulus.

S26, the anode is formed on the hole transport layer.

In addition, the quantum dot light-emitting device may also include other functional films, such as a hole injection layer, which will not be described in detail here.

Specifically, a full-color quantum dot light-emitting device may also be manufactured by adopting the manufacturing method provided by the embodiment of the present disclosure, and the specific manufacturing process for patterning a monochromatic light-emitting layer is as follows:

the light-emitting layer on the hole transport layer specifically includes: a monochromatic light-emitting layer is formed on the hole transport layer by adopting a monochromatic quantum dot material;

and making the cross-linking group of the quantum dot material cross-linked with the modifying group of the hole transport material by adopting the set external stimulus specifically includes: a corresponding area of the monochromatic light-emitting layer is irradiated with ultraviolet light under the shielding of a mask plate, so that the cross-linking group of the monochromatic quantum dot material in the corresponding area is cross-linked with the modifying group of the hole transport material; and the monochromatic light-emitting layer is cleaned, and an area shielded by the mask plate is removed to obtain a graphical monochromatic light-emitting layer.

Figure 13:
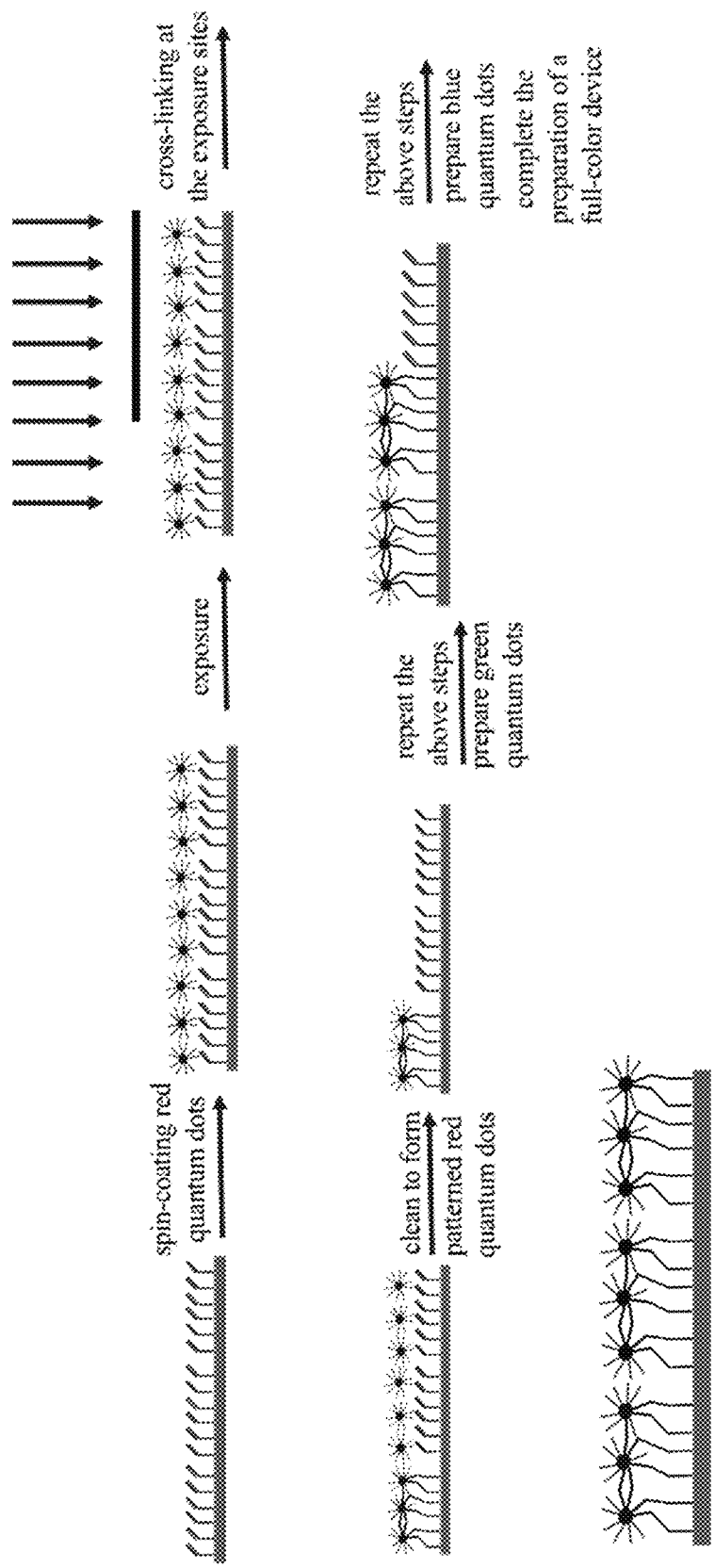
FIG. 13 is a schematic diagram of steps for manufacturing a full-color quantum dot light-emitting device provided by an embodiment of the present disclosure.

By repeating the above steps, patterns of monochromatic light-emitting layers of other colors can be made. Specifically, as shown in FIG. 13, red quantum dots can be spin-coated on the hole transport layer; after exposure by means of the shielding of the mask plate, the exposed red quantum dots are cross-linked with the hole transport material; after cleaning, the red quantum dots which are not cross-linked are washed away, leaving the red quantum dots at the cross-linking sites; after that, green quantum dots can be manufactured by repeating the above steps, and blue quantum dots can be manufactured by repeating the above steps again, so as to complete the preparation of a full-color device.

The manufacturing process of the quantum dot light-emitting device will be described in detail by taking the upright device structure as an example, including the following steps.

(1) A substrate with a formed anode layer is cleaned. Specifically, conductive glass can be cleaned with isopropanol, water, acetone and ultrasonic waves respectively, and treated with ultraviolet irradiation for 5-10 min.

(2) A hole injection layer is manufactured. Specifically, the hole injection layer can be prepared on the conductive glass through spin-coating, vapor deposition, ink-jet printing, etc. PEDOT:PSS 4083 (poly 3,4-ethylenedioxythiophene/polystyrene sulfonate) or other compounds can be used to make the hole injection layer. The film forming temperature of PEDOT is 130° C.-150° C., and the rotating speed of a spin-coater is set at 500-2500 rpm to adjust the thickness of the film.

(3) A hole transport layer is manufactured. Specifically, the hole transport layer can be prepared on the conductive glass through spin-coatinging, vapor deposition, ink-jet printing, etc.

(4) A light-emitting layer is manufactured. Specifically, the light-emitting layer can be prepared on the conductive glass through spin-coatinging, vapor deposition, ink-jet printing, etc. Specifically, a specific manufacturing process of a quantum dot material for forming the light-emitting layer is as follows.

(a) Preparation of a CdSe core: 0.4 mmol of CdO, 3.2 mmol of OA and 10 mL of ODE are added into a 50 mL three-necked round-bottom flask, heated at 120° C., vacuumized for 1 h, and introducing nitrogen and then the temperature is raised to 240° C., so that the solution in the three-necked round-bottom flask is clear and transparent; 1 g of TOP and 3 g of hexadecylamine are added, then the temperature is reduced to 150° C., vacuumized for 30 min, nitrogen is introduced, and the temperature is raised to 280° C.; a clear solution of TOP-Se (2 mmol of Se, 2 mL of TOP and 2.5 mL of ODE are stirred in a glove box to obtain a yellow and transparent solution) is quickly introduced, the temperature is maintained for 3 min, then it is quickly cooled to room temperature, and extracted with a methanol/chloroform solution with a volume ratio of 3:1 for many times, so that the quantum dots obtained are dispersed in chloroform for later use.

(b) Preparation of a ZnS shell precursor: 0.3 mmoL of $Zn(Ac)_2$, 1 mmol of DDT, 6 mL of ODE and 4 mL of OLA are added into a three-necked round-bottom flask, and the process of stirring at 90° C., heating, vacuumizing, and nitrogen introduction is conducted for three times for later use.

(c) Shell coating: 2 mL of CdSe chloroform solution, 2 mL of ODE and 200 μL of OA are added into a three-necked round-bottom flask, the process of vacuumizing at 120° C. and nitrogen replacement is conducted for three times, then the temperature is raised to 240° C., and the ZnS shell precursor is transferred to a main reaction system at 1.5 mL/h.

(d) Cleaning: in order to completely remove free ligands, the cleaning process is divided into three steps: ① 100 mL of acetone/methanol mixed solution with a volume ratio of 7:3 is added into a three-necked round bottom flask filled with a quantum dot solution, magnetically stirred at 60° C. for 10 min, and centrifuged to obtain precipitate; ② in a three-necked round-bottom flask, the precipitate is completely dispersed in 20 mL of toluene, then 100 mL of acetone/methanol mixed solution is added with a volume ratio of 3:7, magnetically stirred at 60° C. for 10 min, and centrifuged to obtain precipitate; and ③ the precipitate is completely dispersed in 20 mL of toluene, the mixture is added into a three-necked round-bottom flask, 20 mL of glacial acetic acid and 70 mL of methanol are added, stirred at 70° C. for 10 min, centrifuged to obtain precipitate, the precipitate is put into a vacuum drying oven to be dried at 60° C., and it is ground into powder for later use.

(e) Ligand exchange of the quantum dot material: 5 ml n-octane quantum dot solution of 20 mg/ml is prepared in a three-necked round-bottom flask, the process of stirring at 80° C., heating, vacuumizing and nitrogen introduction is conducted for three times, then 5 ml n-octane solution of ligand molecules of 60 mg/ml is introduced, reacts for 4 hours, and then step (d) is repeated to thoroughly remove free ligands and dissolved in n-octane for later use.

The quantum dot material solution formed in the above step (e) is directly used to form a film of the light-emitting layer on the conductive glass through spin-coating, vapor deposition, ink-jet printing, etc., that is, ligand exchange first and film formation later.

Another way is to use the quantum dot solution without ligand exchange formed in the above step (d) to directly form the film of the light-emitting layer on the conductive glass through spin-coating, vapor deposition, ink-jet printing, etc., and then coat a layer of solution containing ligand molecules for ligand exchange, that is, film formation first and ligand exchange later.

Specifically, film formation first and ligand exchange later specifically includes: the 20 mg/ml quantum dot n-octane solution is spin-coated on the substrate, dried at 80-120° C. to form a film, the quantum dot film is covered with an acetonitrile solution of 1%-5% by volume of cross-linkable ligands, standing is conducted for 30-120 s to allow ligand exchange of the quantum dot film, and then the substrate is washed for three times with acetonitrile under the condition of dynamic spin-coating to wash away unreacted ligands and exchanged original ligands.

(5) The hole transport material is cross-linked with the quantum dot material. Specifically, the light-emitting layer and the hole transport layer can be cross-linked by annealing or photo-cross-linking. For example, under the irradiation of G line or I line, a carbon-carbon double bond of the quantum dot ligand and a carbon-carbon double bond of the hole transport material can be broken and then cross-linked. After cross-linking, the light-emitting layer and the hole transport layer are linked by chemical bonds, which greatly improves the transmission efficiency of holes between the hole transport layer and the light-emitting layer.

(6) An electron transport layer is manufactured. Specifically, a zinc oxide nanoparticle film or a zinc oxide sol-gel film can be manufactured on the conductive glass. Specifically, a manufacturing process of the zinc oxide nanoparticle film is as follows: for example, 90-120 μL of zinc oxide nanoparticles of 10-30 mg/mL is dripped onto the conductive glass, spin-coated to form a film by setting the rotating speed of a spin-coatinger at 500-2500 rpm so as to adjust the thickness of the zinc oxide film, and the film is obtained at room temperature or under heating conditions (25-120° C.). Particularly, a specific process of adopting the sol-gel film is as follows: for example, 2 g of zinc acetate is added to a solvent containing 10 mL of ethanolamine and n-butanol, spin-coated to form a film under the rotating speed of 1000-4000 rpm, and the film is obtained by heating at a hot stage at 180-250° C. The material of the electron transport layer can also be ion-doped zinc oxide nanoparticles, such as Mg, In, Al and Ga doped zinc oxide nanoparticles.

(7) A cathode is manufactured. Specifically, the cathode can be formed through the evaporation of an Al film or sputtering of an IZO film.

(8) Packaging is conducted. Under ultraviolet excitation, the quantum dot light-emitting device is packaged by adding a packaging cover plate and introducing an ultraviolet curing adhesive.

Based on the same inventive concept, an embodiment of the present disclosure also provides a display apparatus, including the above quantum dot light-emitting device provided by the embodiment of the present disclosure. The display apparatus may be any product or component with a display function, such as a mobile phone, a tablet computer, a television, a display, a notebook computer, a digital photo frame, and a navigator. One can refer to the embodiments of the quantum dot light-emitting device described above for the implementation of the display apparatus, which will not be repeated here.

According to the hole transport material, the quantum dot light-emitting device and the manufacturing method thereof and the display apparatus provided by the embodiments of the present disclosure, a surface of the quantum dot is modified with the ligand which can be cross-linked with the modifying group of the hole transport material, that is, the cross-linking group in the ligand, so that when the quantum dot light-emitting device is manufactured, the cross-linking group of the quantum dot material is cross-linked with the modifying group of the hole transport material under the set external stimulus, which increases the coupling degree between the light-emitting layer and the hole transport layer and weakens an interface structure between the light-emitting layer and the hole transport layer, thus facilitating carrier transmission. Under the condition of not sacrificing the transmission rate of electrons, hole injection is increased to the greatest extent, so as to regulate the injection balance of carriers, improve the carrier recombination rate of the quantum dot light-emitting device, and further improve the luminous efficiency and other device performances of the quantum dot light-emitting device. Moreover, the increase of hole injection will reduce the aggregation of carriers at an interface, thereby improving the stability of the device.

Obviously, those skilled in the art can make various changes and modifications to the present disclosure without departing from the spirit and scope of the present disclosure. Thus, the present disclosure is also intended to include such modifications and variations if they fall within the scope of the claims of the present disclosure and their equivalents.

What is claimed is:

1. A quantum dot light-emitting device, comprising an anode, a hole transport layer, a light-emitting layer, an electron transport layer and a cathode disposed in a stacked mode, wherein the hole transport layer comprises a hole transport material comprising a body of the hole transport material and a modifying group connected with the body of the hole transport material, wherein the modifying group is configured to be cross-linked with a cross-linking group of a quantum dot material under a set external stimulus, wherein the light-emitting layer comprises a quantum dot material comprising a quantum dot and a ligand connected with the quantum dot; and the ligand comprises a coordinating group bonded with the quantum dot, a solubilizing group connected with the coordinating group, and a cross-linking group connected with the solubilizing group, wherein the cross-linking group is cross-linked with the modifying group of the hole transport material;

wherein the quantum dot material and the hole transport material are arranged in different layers;

wherein a molecular formula of the ligand of the quantum dot material is as follows:

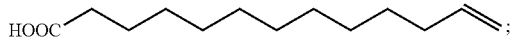

a molecular formula of the hole transport material is as follows:

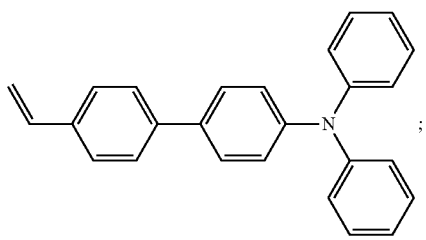 [SMILES: C=Cc1ccc(-c2ccc(N(c3ccccc3)c3ccccc3)cc2)cc1]

and a molecular formula after the ligand of the quantum dot material is cross-linked with the hole transport material is as follows:

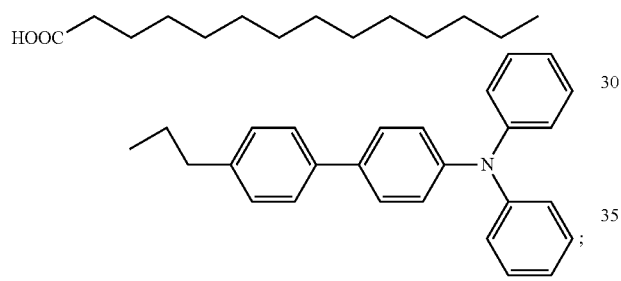

or, a molecular formula of the ligand of the quantum dot material is as follows:

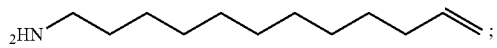

a molecular formula of the hole transport material is as follows:

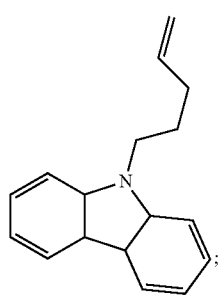 [SMILES: C=CCCCN1C2C=CC=CC2C2C=CC=CC21]

and a molecular formula after the ligand of the quantum dot material is cross-linked with the hole transport material is as follows:

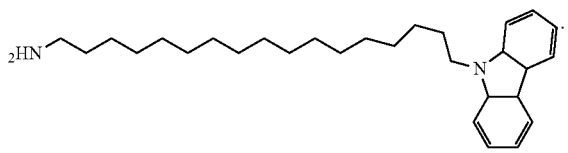

or, a molecular formula of the ligand of the quantum dot material is as follows:

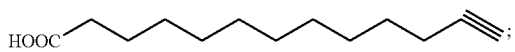

a molecular formula of the hole transport material is as follows:

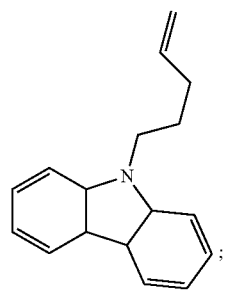 [SMILES: C=CCCCN1C2C=CC=CC2C2C=CC=CC21]

and a molecular formula after the ligand of the quantum dot material is cross-linked with the hole transport material is as follows:

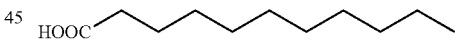

or, a molecular formula of the ligand of the quantum dot material is as follows:

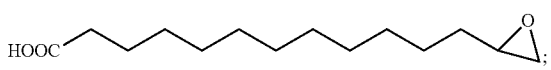 [SMILES: O=C(O)CCCCCCCCCCCC1CO1]

a molecular formula of the hole transport material is as follows:

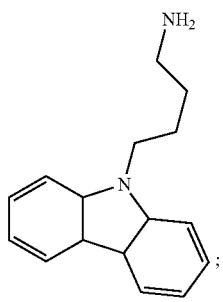 [SMILES: NCCCCN1C2C=CC=CC2C2C=CC=CC21]

and a molecular formula after the ligand of the quantum dot material is cross-linked with the hole transport material is as follows:

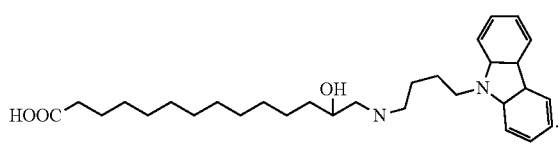 [SMILES: O=C(O)CCCCCCCCCCCC(O)CNCCCCN1C2C=CC=CC2C2C=CC=CC21]

or, a molecular formula of the ligand of the quantum dot material is as follows:

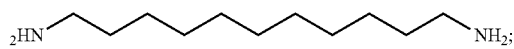

a molecular formula of the hole transport material is as follows:

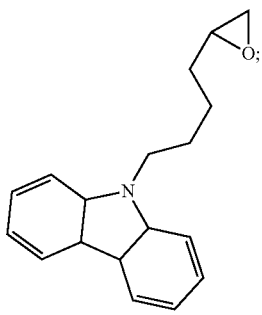 [SMILES: C1=CC2C3C=CC=CC3N(CCCCC3CO3)C2C=C1]

and a molecular formula after the ligand of the quantum dot material is cross-linked with the hole transport material is as follows:

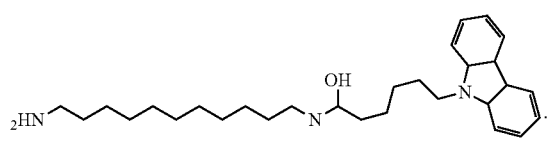

or, a molecular formula of the ligand of the quantum dot material is as follows:

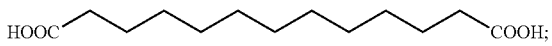

a molecular formula of the hole transport material is as follows:

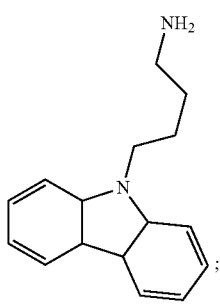 [SMILES: NCCCCN1C2C=CC=CC2C2C=CC=CC21]

and a molecular formula after the ligand of the quantum dot material is cross-linked with the hole transport material is as follows:

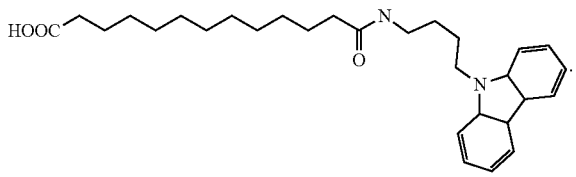 [SMILES: O=C(O)CCCCCCCCCCCC(=O)NCCCCN1C2C=CC=CC2C2C=CC=CC21]

2. The quantum dot light-emitting device according to claim 1, wherein the cross-linking group comprises at least one of a double bond group, a triple bond group or an epoxy group.

3. The quantum dot light-emitting device according to claim 2, wherein the cross-linking group comprises at least one of alkenyl group, alkynyl group, ester group, aldehyde group, carbonyl group, azide, cyano group, amino group, carboxyl group, mercapto group, ethylene oxide, propylene oxide, butylene oxide or pentane oxide.

4. The quantum dot light-emitting device according to claim 1, wherein the solubilizing group comprises at least one of ethyl, n-butyl, tert-butyl, n-octyl, tert-butyl phenyl, methoxy or n-butoxy.

5. The quantum dot light-emitting device according to claim 1, wherein the coordinating group comprises at least one of amino, polyamino, hydroxyl, polyhydroxy, mercapto, polythiol, thioether, polythioether, phosphine or phosphine oxide.

6. The quantum dot light-emitting device according to claim 1, further comprising a substrate, wherein the anode, the hole transport layer, the light-emitting layer, the electron transport layer and the cathode are sequentially stacked on the substrate; or further comprising a substrate, wherein the cathode, the electron transport layer, the light-emitting layer, the hole transport layer and the anode are sequentially stacked on the substrate.

7. A display apparatus, comprising a quantum dot light-emitting device, wherein the quantum dot light-emitting device comprises an anode, a hole transport layer, a light-emitting layer, an electron transport layer and a cathode disposed in a stacked mode, wherein the hole transport layer comprises a hole transport material comprising a body of the hole transport material and a modifying group connected with the body of the hole transport material, wherein the modifying group is configured to be cross-linked with a cross-linking group of a quantum dot material under a set external stimulus, wherein the light-emitting layer comprises a quantum dot material comprising a quantum dot and a ligand connected with the quantum dot; and the ligand comprises a coordinating group bonded with the quantum dot, a solubilizing group connected with the coordinating group, and a cross-linking group connected with the solubilizing group, wherein the cross-linking group is cross-linked with the modifying group of the hole transport material;

wherein the quantum dot material and the hole transport material are arranged in different layers;

wherein a molecular formula of the ligand of the quantum dot material is as follows:

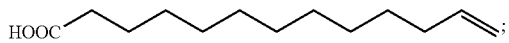

a molecular formula of the hole transport material is as follows:

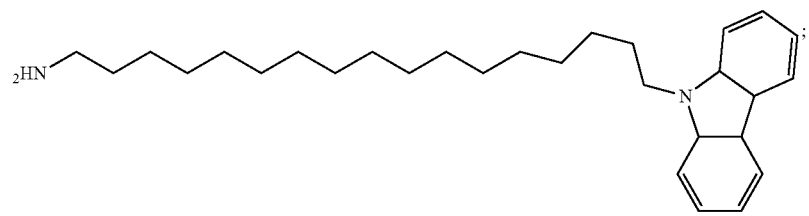

and a molecular formula after the ligand of the quantum dot material is cross-linked with the hole transport material is as follows:

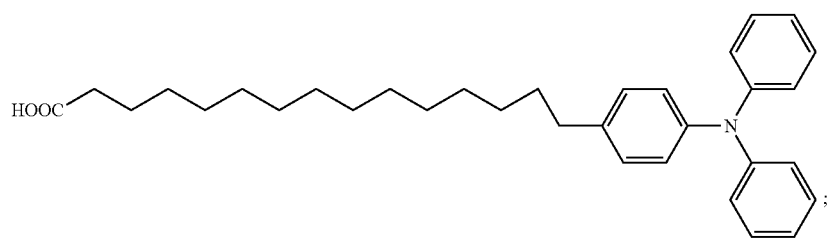 [SMILES: O=C(O)CCCCCCCCCCCCCCc1ccc(N(c2ccccc2)c2ccccc2)cc1]

or, a molecular formula of the ligand of the quantum dot material is as follows:

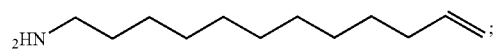

a molecular formula of the hole transport material is as follows:

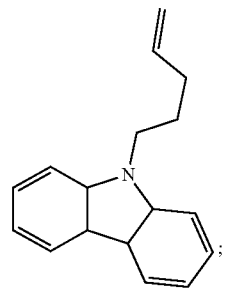 [SMILES: C=CCCCN1C2C=CC=CC2C2C=CC=CC21]

and a molecular formula after the ligand of the quantum dot material is cross-linked with the hole transport material is as follows:

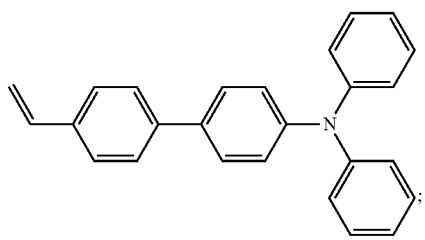

or, a molecular formula of the ligand of the quantum dot material is as follows:

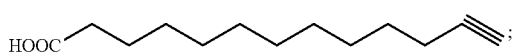

a molecular formula of the hole transport material is as follows:

31

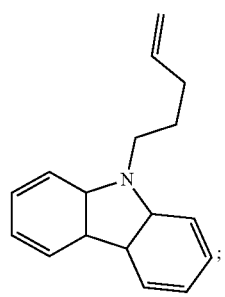 [SMILES: C=CCCCN1C2C=CC=CC2C2C=CC=CC21]

and a molecular formula after the ligand of the quantum dot material is cross-linked with the hole transport material is as follows:

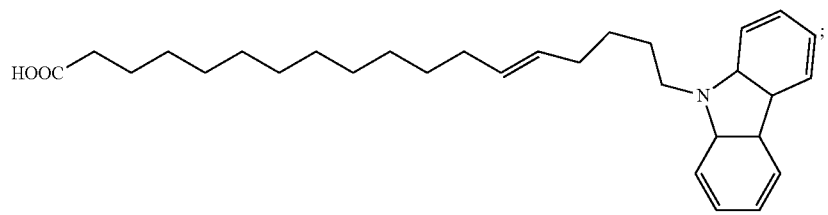 [SMILES: O=C(O)CCCCCCCCCCC/C=C/CCCCN1C2C=CC=CC2C2C=CC=CC21]

or,
a molecular formula of the ligand of the quantum dot material is as follows:

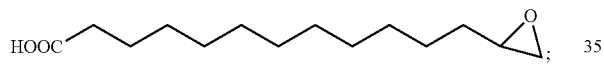

a molecular formula of the hole transport material is as follows:

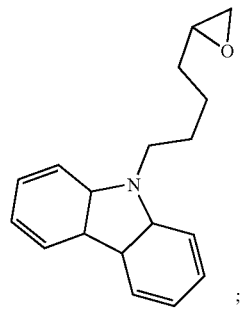 [SMILES: C1=CC2C3C=CC=CC3N(CCCCC3CO3)C2C=C1]

and a molecular formula after the ligand of the quantum dot material is cross-linked with the hole transport material is as follows:

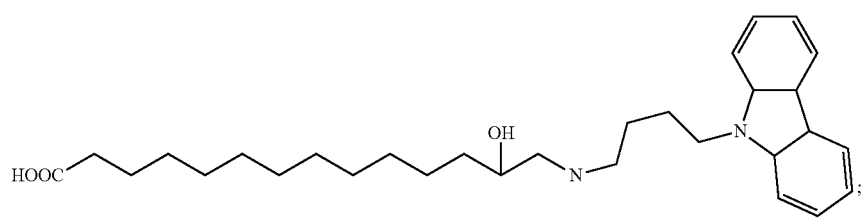 [SMILES: O=C(O)CCCCCCCCCCCC(O)CNCCCCN1C2C=CC=CC2C2C=CC=CC21]

32 or,
a molecular formula of the ligand of the quantum dot material is as follows:

a molecular formula of the hole transport material is as follows:

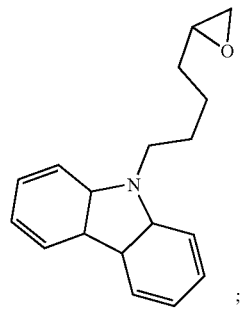 [SMILES: C1=CC2C3C=CC=CC3N(CCCCC3CO3)C2C=C1]

and a molecular formula after the ligand of the quantum dot material is cross-linked with the hole transport material is as follows:

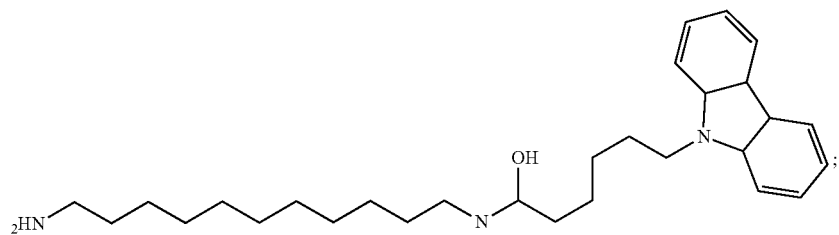
or
a molecular formula of the ligand of the quantum dot material is as follows:
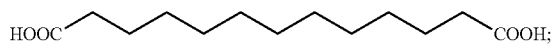 [SMILES: O=C(O)CCCCCCCCCCCC(=O)O]
a molecular formula of the hole transport material is as follows:
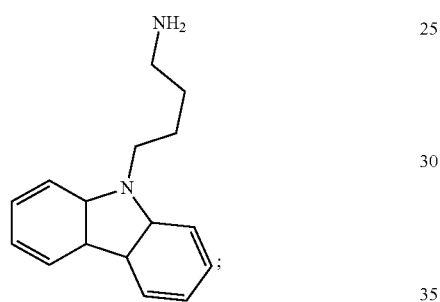
and a molecular formula after the ligand of the quantum dot material is cross-linked with the hole transport material is as follows:
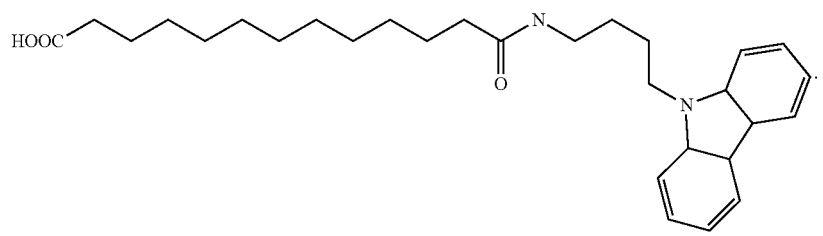 [SMILES: O=C(O)CCCCCCCCCCCC(=O)NCCCCN1C2C=CC=CC2C2C=CC=CC21]
* * * * *